(12) United States Patent
Adden et al.

(10) Patent No.: US 9,394,376 B2
(45) Date of Patent: *Jul. 19, 2016

(54) CELLULOSE ETHERS AND THEIR USE

(75) Inventors: Roland Adden, Walsrode (DE); Meinolf Brackhagen, Walsrode (DE); Matthias Knarr, Nienburg (DE); Jin Zhao, Midland, MI (US)

(73) Assignee: Dow Global Technologies LLC

( * ) Notice: Subject to any disclaimer, the term of this patent is extended or adjusted under 35 U.S.C. 154(b) by 561 days.

This patent is subject to a terminal disclaimer.

(21) Appl. No.: 13/825,697

(22) PCT Filed: Oct. 6, 2011

(86) PCT No.: PCT/US2011/055050
§ 371 (c)(1),
(2), (4) Date: Mar. 22, 2013

(87) PCT Pub. No.: WO2012/051035
PCT Pub. Date: Apr. 19, 2012

(65) Prior Publication Data
US 2013/0236512 A1    Sep. 12, 2013

Related U.S. Application Data

(60) Provisional application No. 61/392,079, filed on Oct. 12, 2010.

(51) Int. Cl.
*C08B 11/02* (2006.01)
*C08B 11/193* (2006.01)
*C08L 1/28* (2006.01)
*A61J 3/07* (2006.01)
*A61K 9/48* (2006.01)
*A61K 47/38* (2006.01)

(52) U.S. Cl.
CPC .............. *C08B 11/02* (2013.01); *A61K 9/4866* (2013.01); *A61K 47/38* (2013.01); *C08B 11/193* (2013.01); *C08L 1/284* (2013.01); *A61J 3/077* (2013.01)

(58) Field of Classification Search
CPC ....... A61J 3/077; A61K 47/38; A61K 9/4866; C08B 11/02; C08B 11/193; C08L 1/284
See application file for complete search history.

(56) References Cited

U.S. PATENT DOCUMENTS

| 2,526,683 | A |   | 10/1950 | Murphy |  |
|---|---|---|---|---|---|
| 3,493,407 | A |   | 2/1970 | Greminger et al. |  |
| 4,001,211 | A | * | 1/1977 | Sarkar .................. | A61K 9/4816 |
|  |  |  |  |  | 106/162.82 |
| 4,316,982 | A |   | 2/1982 | Holst et al. |  |
| 4,550,161 | A |   | 10/1985 | Felcht et al. |  |
| 6,228,416 | B1 |   | 5/2001 | Reibert et al. |  |
| 6,235,893 | B1 | * | 5/2001 | Reibert .................. | A23L 1/0534 |
|  |  |  |  |  | 264/140 |
| 6,410,050 | B1 |   | 6/2002 | Yang |  |
| 7,402,668 | B2 |   | 7/2008 | Dannhorn et al. |  |
| 2004/0242862 | A1 |   | 12/2004 | Hammes et al. |  |
| 2005/0240016 | A1 |   | 10/2005 | Schlesiger et al. |  |
| 2007/0026063 | A1 | * | 2/2007 | Maruyama ........... | A61K 9/2866 |
|  |  |  |  |  | 424/464 |
| 2008/0262216 | A1 |   | 10/2008 | Hayakawa et al. |  |
| 2009/0140452 | A1 |   | 6/2009 | DeRosa et al. |  |
| 2009/0218711 | A1 |   | 9/2009 | Dasher et al. |  |

FOREIGN PATENT DOCUMENTS

| EP | 134465 A1 | 3/1985 |
|---|---|---|
| EP | 210917 A2 | 4/1987 |
| EP | 714656 A1 | 5/1996 |
| EP | 1983004 A1 | 10/2008 |
| WO | 00/32637 | 6/2000 |
| WO | 02/94882 A1 | 11/2002 |
| WO | 2007/078015 A1 | 7/2007 |
| WO | 2008/050209 A1 | 5/2008 |

OTHER PUBLICATIONS

Ackman, Fundamental Groups in the Response of Flame Ionization Detectors to Oxygenated Aliphatic Hydrocarbons, Journal of Gas Chromatography, (1964), pp. 173-179.
Addison, et al., Flame Ionization Detector Molar Responses for Methyl Esters of Some Polyfunctional Metabolic Acids, Journal of Gas Chromatography, 6, (1968), pp. 135-138.
Sweet, et al., Quantitative Analysis by Various G.L.C. Response-Factor Theories for Partially Methylated and Partially Ethylated Alditol Acetates, Carbohydrate Research, 40, (1975), pp. 217-225.
Bartelmus, Analysis of Cellulose ether groups, Z. Anal. Chem., 286, (1977), pp. 161-190.
Sarkar, Thermal Gelation Properties of Methyl and Hydroxypropyl Methylcellulose, Journal of Applied Polymer Science, 24, (1979) pp. 1073-1087.
Lindberg, et al., Distribution of Substituents in O-Ethyl-O-(2-Hydroxyethyl)Cellulose, Carbohydrate Research, 176, (1988) pp. 137-144.
Haque, et al., Thermogelation of methylcellulose. Part I: molecular structures and processes, Carbohydrate Polymers, 22, (1993) pp. 161-173.
Haque, et al., Thermogelation of methylcellulose. Part II: effect of hydroxypropyl substituents, Carbohydrate Polymers, 22, (1993) pp. 175-186.
Sarkar, Kinetics of thermal gelation of methylcellulose and hydroxypropylmethylcellulose in aqueous solutions, Carbohydrate Polymers, 26, (1995), pp. 195-203.

(Continued)

*Primary Examiner* — Michael B Pallay

(57) ABSTRACT

Cellulose ethers are described herein which are useful in capsules or in coatings for dosage forms. In these cellulose ethers the ether substituents are methyl groups, hydroxyalkyl groups, and optionally alkyl groups being different from methyl, the cellulose ether has an MS (hydroxyalkyl) of 0.05 to 1.00, and hydroxy groups of anhydroglucose units are substituted with methyl groups such that $[s_{23}/s_{26} - 0.2*MS(\text{hydroxyalkyl})]$ is 0.35 or less, wherein $s_{23}$ is the molar fraction of anhydroglucose units wherein only the two hydroxy groups in the 2- and 3-positions of the anhydroglucose unit are substituted with methyl groups and wherein $s_{26}$ is the molar fraction of anhydroglucose units wherein only the two hydroxy groups in the 2- and 6-positions of the anhydroglucose unit are substituted with methyl groups.

13 Claims, 1 Drawing Sheet

(56) References Cited

OTHER PUBLICATIONS

Hussain, A thermorheological investigation into the gelation and phase separation of hydroxypropyl methylcellulose aqueous systems, Polymer, 43 (2002) pp. 5623-5628.

Cole, et al., In Vitro and in Vivo Pharmacoscintigraphic Evaluation of Ibuprofen Hypromellose and Gelatin Capsules, Pharmaceutical Research, 21, (2004) pp. 793-798.

Silva, et al., Aggregation and gelation in hydroxypropylmethyl cellulose aqueous solutions, Journal of Colloid and Interface Science, 327, (2008) pp. 333-340.

Bodvik, et al., Aggregation and network formation of aqueous methylcellulose and hydroxypropylmethylcellulose solutions, Colloids and Surfaces, 354, (2010), pp. 162-171.

* cited by examiner

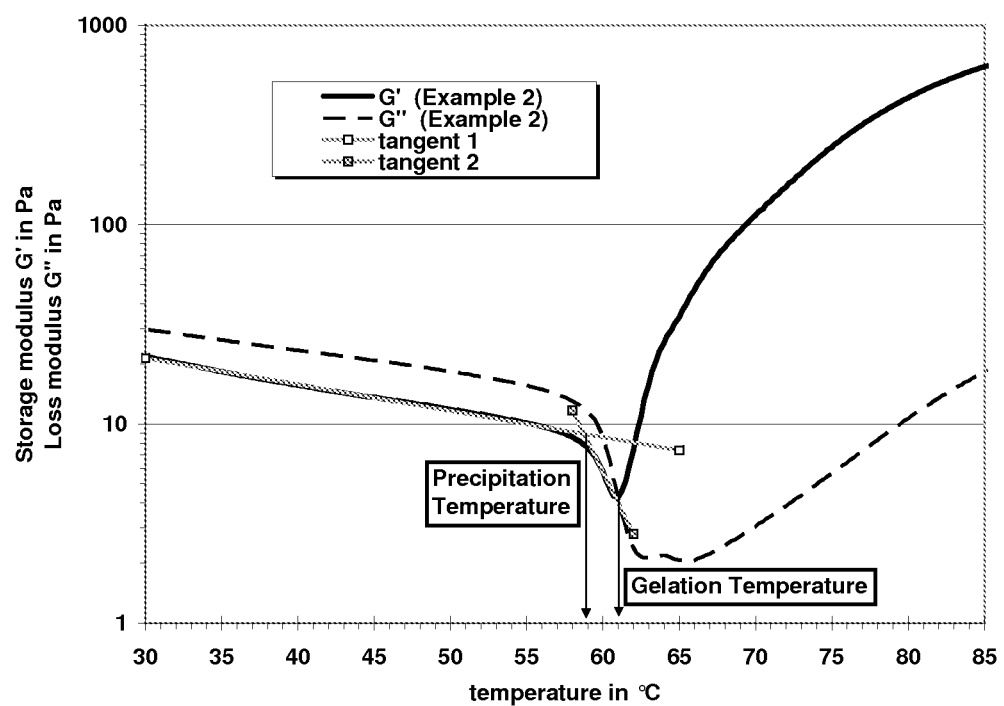

CELLULOSE ETHERS AND THEIR USE

CROSS REFERENCE TO RELATED APPLICATIONS

This application is a 35 USC §371 national phase filing of PCT/US2011/055050, filed Oct. 6, 2011, which claims the benefit of U.S. Application No. 61/392,079, filed Oct. 12, 2010.

FIELD

This invention relates to novel cellulose ethers and their use in capsules or in coatings for dosage forms.

BACKGROUND

Capsules are well-known dosage forms that normally consist of a shell filled with one or more specific substances. The shell may be a soft or a hard stable shell comprising film-forming polymer(s) such as gelatin, modified starches or modified celluloses. Hard capsules are generally manufactured by using a dip molding process. In this process, pin molds are dipped into a film forming composition. By gelling the film forming polymer on the pin, a film is formed that is subsequently dried on the pin to obtain a capsule shell. The shells are then stripped off the pins and cut to a desired length. Thus, capsules caps and bodies are obtained that can later be filled with a substance and joined such that a filled capsule is obtained. When using this type of dip molding process, it is necessary to ensure that the dipping composition adheres to the pin surface and quickly gels, once the pins are withdrawn from the dipping bath. This avoids that the composition flows on the pins surface so as to achieve the desired shell or film thickness distribution to manufacture capsules. When using gelatin as the film forming polymer, the dipping compositions gel with cooling. The same gelling behavior is shown by mixtures of methyl celluloses and gelling agents. Both these types of film forming polymers may be processed on conventional devices for manufacturing hard gelatin capsules. Methylcellulose and hydroxypropyl methylcellulose have "thermoreversible gelation properties". Described specifically, when an aqueous solution of methylcellulose or hydroxypropyl methylcellulose is heated, de-hydration of the hydrophobic methoxyl groups localized in the molecule occurs and it turns into a hydrous gel. When the resulting gel is cooled, on the other hand, the hydrophobic methoxyl groups are re-hydrated, whereby the gel returns to the original aqueous solution.

U.S. Pat. No. 2,526,683 discloses a process for preparing methyl cellulose medicinal capsules by a dip coating process. The process consists of dipping a capsule forming pin pre-heated to 40° C.-85° C. into a methyl cellulose composition maintained at a temperature below the temperature where gelation begins, withdrawing the pins and placing the pins in ovens at temperatures above the gelation temperature and drying the film. When the hot pins are dipped into the composition, the composition gels on the surface of the pin and as the pin is withdrawn, a film of gelled liquid of a certain thickness is formed on the pin. The pin is typically placed in the oven to dry. This technique is conventionally named "thermogelation". The dry capsule is then stripped, cut to size and the body and caps are fitted together.

Due to the thermoreversible gelation properties of methylcellulose and hydroxypropyl methylcellulose, these cellulose ethers have also been suggested as film-forming coatings on dosage forms, such as tablets, granules, pellets, caplets, lozenges, suppositories, pessaries or implantable dosage forms. However, methyl cellulose is quite hydrophobic; its hydrophobic properties are not compatible with some of the common capsule ingredients or fillings. Moreover, for some applications, capsules made from methyl cellulose do not dissolve fast enough in water.

U.S. Pat. No. 3,493,407, discloses the use of non-thermal gelling dip-molding compositions of some hydroxyalkyl methyl celluloses in aqueous solvents. The pins must be kept in rotation for more than half an hour to obtain capsules with a regular shape.

U.S. Pat. No. 4,001,211 discloses improved thermogelling compositions based on a blend of methyl cellulose (MC) and hydroxypropyl methyl cellulose (HPMC).

However, the more recent patent publication WO 2008/050209 A1 discloses that the compositions and processes described above did not make it possible to obtain high-performance manufacturing of hard capsules both with regard to speed, dissolution properties and with regard to overall quality. It further discusses that capsules manufactured by a combination of HPMC with gelling agents have very poor visual quality and dissolution properties since they are sensitive to cations and to pH.

To overcome the disadvantages of the prior art, WO 2008/050209 suggests the use of an aqueous composition for the manufacture of hard capsules which comprises, in an aqueous solvent, 15-25% by weight, based on the total weight of the aqueous composition, of a hydroxypropyl methyl cellulose having a methoxy content of 27.0-30.0% (w/w), a hydroxypropoxy content of 4.0-7.5% (w/w) and a viscosity of 3.5-6.0 cPs as a 2% weight solution in water at 20° C. The use of this type of hydroxypropyl methyl cellulose provides advantages in the manufacture of capsules, compared to other hydroxypropyl methyl celluloses; aqueous solutions of the disclosed hydroxypropyl methyl cellulose have a lower gelation temperature than hydroxypropyl methyl celluloses having a methoxy content of 28.0-30.0% (w/w), a hydroxypropoxy content of 7.0-12% (w/w) and a corresponding viscosity. In the dip coating process for preparing capsules, it is common practice to heat the aqueous solution of the hydroxypropyl methyl cellulose to a temperature which is only a few degrees Celsius below its gelation temperature before pins are dipped into the aqueous solution of the hydroxypropyl methyl cellulose. Accordingly, a high gelation temperature is not desirable because this requires an unduly high amount of time and energy to heat the aqueous solution of the hydroxypropyl methyl cellulose. Unfortunately, even the gelation temperature of the hydroxypropyl methyl cellulose disclosed in WO 2008/050209 is still higher than desired by many capsule manufacturers. Moreover, hydroxyalkyl methylcelluloses are known to have a low storage modulus, compared to methyl cellulose. Hydroxyalkyl methylcelluloses which exhibit a low storage modulus do not form strong gels. High concentrations are needed to form even weak gels (Hague, A; Richardson, R. K.; Morris, E. R., Gidley, M. J and Caswell, D. C in Carbohydrate Polymers 22 (1993) p. 175; and Hague, A. and Morris, E. R. in Carbohydrate Polymers 22 (1993) p. 161). For example, at the same concentration of 2 wt.-%, at elevated temperatures the maximum storage modulus of a METHOCEL™ K4M HPMC is typically less than about 100 Pa, whereas that of a METHOCEL™ A4M methylcellulose is typically above about 1000 Pa. It is concluded that the hydroxyalkyl substituents inhibit intermolecular associations.

Accordingly, one object of the present invention is to provide novel cellulose ethers which are useful for producing capsules or coatings for dosage forms.

A preferred object of the present invention is to provide novel cellulose ethers which have a lower gelation temperature in aqueous solutions than known hydroxyalkyl methyl celluloses of the same viscosity and concentration in aqueous solutions.

Moreover, another preferred object of the present invention is to provide novel cellulose ethers which have a higher storage modulus than known hydroxyalkyl methylcelluloses.

SUMMARY

Surprisingly, novel cellulose ethers have been found which have a lower gelation temperature in an aqueous solution than known hydroxyalkyl methylcelluloses. Accordingly, the novel cellulose ethers of the present invention are very useful for producing capsules or for producing coatings of dosage forms, particularly by a thermogelation process.

One aspect of the present invention is a cellulose ether wherein
the ether substituents are methyl groups, hydroxyalkyl groups, and optionally alkyl groups being different from methyl,
the cellulose ether has an MS (hydroxyalkyl) of 0.05 to 1.00, and
hydroxy groups of anhydroglucose units are substituted with methyl groups such that [s23/s26−0.2*MS(hydroxyalkyl)] is 0.35 or less,
wherein s23 is the molar fraction of anhydroglucose units wherein only the two hydroxy groups in the 2- and 3-positions of the anhydroglucose unit are substituted with a methyl group and
wherein s26 is the molar fraction of anhydroglucose units wherein only the two hydroxy groups in the 2- and 6-positions of the anhydroglucose unit are substituted with a methyl group.

Another aspect of the invention is an aqueous composition for the manufacture of capsules or coatings of dosage forms which comprises from 7 to 40 weight percent of the above-mentioned cellulose ether, based on the total weight of the aqueous composition.

Yet another aspect of the invention is a process for coating a dosage form which comprises the step of contacting an aqueous composition comprising the above-mentioned cellulose ether with the dosage form.

Yet another aspect of the invention is a process for the manufacture of capsules which comprises the step of contacting an aqueous composition comprising the above-mentioned cellulose ether with dipping pins.

Yet another aspect of the invention is a capsule shell comprising the above-mentioned cellulose ether.

Yet another aspect of the invention is a capsule comprising the above-mentioned capsule shell.

Yet another aspect of the invention is a dosage form coated with a composition comprising the above-mentioned cellulose ether.

BRIEF DESCRIPTION OF THE DRAWINGS

FIG. 1 illustrates how to determine the precipitation temperature and the gelation temperature of a cellulose ether of the present invention.

DETAILED DESCRIPTION

In the cellulose ethers of the present invention the ether substituents are methyl groups, hydroxyalkyl groups, and optionally alkyl groups which are different from methyl. The hydroxyalkyl groups can be the same or different from each other. Preferably the cellulose ether comprises one or two kinds of hydroxyalkyl groups, more preferably one or more kinds of hydroxy-$C_{1-3}$-alkyl groups, such as hydroxypropyl and/or hydroxyethyl. Useful optional alkyl groups are, e.g., ethyl or propyl, ethyl being preferred. Preferred ternary cellulose ethers of the present invention are ethyl hydroxypropyl methyl celluloses, ethyl hydroxyethyl methyl celluloses, or hydroxyethyl hydroxypropyl methyl celluloses. Preferred cellulose ethers are hydroxyalkyl methyl celluloses, particularly hydroxy-$C_{1-3}$-alkyl methyl celluloses, such as hydroxypropyl methylcelluloses or hydroxyethyl methylcelluloses.

An essential feature of the novel cellulose ethers is their unique distribution of methyl groups on the anhydroglucose units such that
[s23/s26−0.2*MS(hydroxyalkyl)] is 0.35 or less, preferably 0.32 or less, more preferably 0.30 or less, most preferably 0.27 or less, particularly 0.25 or less, and especially 0.23 or less. Typically [s23/s26−0.2*MS(hydroxyalkyl)] is 0.07 or more, more typically 0.10 or more, and most typically 0.13 or more. More specifically, in the case of hydroxyethyl methylcelluloses the upper limit for [s23/s26−0.2*MS(hydroxyalkyl)] is 0.35; preferably 0.32, more preferably 0.30 and most preferably 0.27. In the case of hydroxypropyl methylcelluloses the preferred upper limit for [s23/s26−0.2*MS(hydroxyalkyl)] generally is 0.30, preferably 0.27; more preferably 0.25 and most preferably 0.23. As used herein, the symbol "*" represents the multiplication operator.

In the ratio s23/s26, s23 is the molar fraction of anhydroglucose units wherein only the two hydroxy groups in the 2- and 3-positions of the anhydroglucose unit are substituted with methyl groups and s26 is the molar fraction of anhydroglucose units wherein only the two hydroxy groups in the 2- and 6-positions of the anhydroglucose unit are substituted with methyl groups. For determining the s23, the term "the molar fraction of anhydroglucose units wherein only the two hydroxy groups in the 2- and 3-positions of the anhydroglucose unit are substituted with methyl groups" means that the 6-positions are not substituted with methyl; for example, they can be unsubstituted hydroxy groups or they can be substituted with hydroxyalkyl groups, methylated hydroxyalkyl groups, alkyl groups different from methyl or alkylated hydroxyalkyl groups. For determining the s26, the term "the molar fraction of anhydroglucose units wherein only the two hydroxy groups in the 2- and 6-positions of the anhydroglucose unit are substituted with methyl groups" means that the 3-positions are not substituted with methyl; for example, they can be unsubstituted hydroxy groups or they can be substituted with hydroxyalkyl groups, methylated hydroxyalkyl groups, alkyl groups different from methyl or alkylated hydroxyalkyl groups.

Formula I below illustrates the numbering of the hydroxy groups in anhydroglucose units. Formula I is only used for illustrative purposes and does not represent the cellulose ethers of the invention; the substitution with hydroxyalkyl groups is not shown in Formula I.

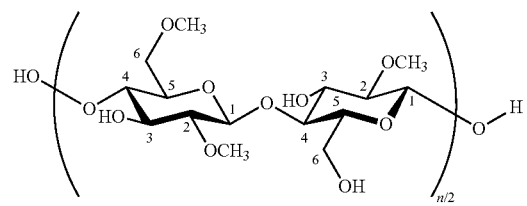

Formula I

The cellulose ether preferably has a DS(methyl) of from 1.2 to 2.2, more preferably from 1.25 to 2.10, and most preferably from 1.40 to 2.00. The degree of the methyl substitution, DS(methyl), of a cellulose ether is the average number of OH groups substituted with methyl groups per anhydroglucose unit. For determining the DS(methyl), the term "OH groups substituted with methyl groups" does not only include the methylated OH groups at the polymer backbone, i.e., that are directly a part of the anhydroglucose unit, but also methylated OH groups that have been formed after hydroxyalkylation.

The cellulose ether has an MS(hydroxyalkyl) of 0.05 to 1.00, preferably 0.07 to 0.80, more preferably 0.08 to 0.70, most preferably 0.10 to 0.60, and particularly 0.10 to 0.50. The degree of the hydroxyalkyl substitution is described by the MS (molar substitution). The MS(hydroxyalkyl) is the average number of hydroxyalkyl groups which are bound by an ether bond per mole of anhydroglucose unit. During the hydroxyalkylation, multiple substitutions can result in side chains.

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion. The DS(methyl) and MS (hydroxyethyl) in hydroxyethyl methylcellulose is effected by Zeisel cleavage with hydrogen iodide followed by gas chromatography. (G. Bartelmus and R. Ketterer, Z. Anal. Chem. 286 (1977) 161-190).

In one aspect of the present invention the viscosity of the cellulose ether is more than 150 mPa·s, preferably from 500 to 200,000 mPa·s, more preferably from 500 to 100,000 mPa·s, most preferably from 1000 to 80,000, particularly from 1000 to 60,000, determined in a 1.5% by weight aqueous solution at 20° C. in a Haake RS600 rheometer with a cone and plate Geometry (CP-60/2°) at 20° C. and at a shear rate of 2.55 s$^{-1}$. The cellulose ethers having such viscosities are useful for a variety of applications, for example as a feedstock material for producing cellulose ethers of low molecular weight which are used in the manufacture of capsules or coatings for dosage forms.

It has surprisingly been found that the preferred embodiments of the cellulose ethers of the present invention which have a viscosity of more than 150 mPa·s, measured in a 1.5 wt. % aqueous solution at 20° C. as defined above, do not have a detectable precipitation temperature as a 1.5 wt. % aqueous solution at atmospheric pressure or have a gelation temperature that is not more than 3 degrees Celsius, preferably not more than 2.5 degrees Celsius, more preferably not more than 2 degree Celsius above the precipitation temperature of the cellulose ether. When a precipitation takes places at elevated temperatures the storage modulus drops down. This precipitation temperature is analyzed from a plot of the log storage modulus G' vs. normal (non-log) temperature as the cross over of two tangents. The first tangent is fitted to the decrease of the storage modulus with increasing temperatures and the second tangent is fitted to the drop of the storage modulus over a temperature region of 1-3° C. The gelation temperature is the temperature at which G'/G''=1, G' being the storage modulus and G'' being the loss modulus of a 1.5 wt.-% aqueous solution of the cellulose ether. FIG. 1 illustrates how to determine the precipitation temperature and the gelation temperature of a cellulose ether of the present invention. In some embodiments of the invention the cellulose ethers even do not have a detectable precipitation temperature as a 1.5 wt.-% aqueous solution at atmospheric pressure. This low difference between gelation temperature and precipitation temperature or the non-detectable precipitation temperature makes the novel cellulose ethers of the present invention highly advantageous as feedstock material for producing low molecular weight cellulose ethers which are used in the manufacture of capsules or coatings for dosage forms. Cellulose ethers of the present invention which have a viscosity of more than 150 mPa·s, determined in a 1.5% by weight aqueous solution at 20° C. and a shear rate of 2.55 s$^{-1}$ and which exhibit the above-mentioned low difference between gelation temperature and precipitation temperature can be partially depolymerized to cellulose ethers of low viscosity which have a low gelation temperature, which makes them very useful for producing capsules or coatings for dosage forms.

To characterize the temperature dependent properties of the precipitation or gelation of a 1.5 weight percent aqueous solution of the cellulose ether, an Anton Paar Physica MCR 501 rheometer (Ostfildem, Germany) with a Cup & Bob set-up (CC-27) and a peltier temperature control system was used in oscillation shear flow. Details of the measurements are described in the Example section.

It has also surprisingly been found that the cellulose ethers of the present invention which have a viscosity of more than 150 mPa·s, determined in a 1.5% by weight aqueous solution at 20° C. and a shear rate of 2.55 s$^{-1}$ as defined above have a surprisingly high gel strength. When an aqueous solution of the cellulose ether is characterized by G'/G''≥1, i.e. when it forms a gel, the gel strength is measured as storage modulus G'. Cellulose ethers of the present invention which have a viscosity of more than 150 mPa·s, determined in a 1.5% by weight aqueous solution at 20° C. and a shear rate of 2.55 s$^{-1}$, generally have a storage modulus G' of at least 50 Pa, preferably at least 100 Pa, more preferably at least 150, and most preferably at least 200 Pa, measured as a 1.5 weight percent aqueous solution at 80° C. Such a storage modulus G' is generally even achieved when the MS(hydroxyalkyl) is within the range of >0.30 and up to 1.00, more typically up to 0.80, most typically up to 0.60. When the MS(hydroxyalkyl) is within the range of 0.05 to 0.30, the cellulose ether of the present invention generally has a storage modulus G' of at least 100 Pa, preferably of at least 150 Pa, more preferably at least 200 Pa, most preferably at least 250 Pa, and in many cases even at least 300 Pa, measured as a 1.5 weight percent aqueous solution at 80° C. Under optimized conditions storage moduli of up to 20,000 Pa, typically of up to 10,000 Pa, and more typically of up to 5,000 Pa, measured as a 1.5 weight percent aqueous solution at 80° C. can be achieved. The gel strength of the cellulose ethers of the present invention, which have a viscosity of more than 150 mPa·s, determined in a 1.5% by weight aqueous solution at 20° C. and a shear rate of 2.55 s$^{-1}$ as defined above, is higher than the gel strength of comparative cellulose ethers having a comparable viscosity and types and percentages of substitution. This makes them highly advantageous as feedstock material for producing low molecular weight cellulose ethers which are used in the manufacture of capsules or coatings for dosage forms since this leads to low molecular weight cellulose ethers which also have good gel strength.

In another aspect of the present invention the viscosity of the cellulose ether is from 2 to 200 mPa·s, preferably from 2 to 100 mPa·s, more preferably from 2.5 to 50 mPa·s, in particular from 3 to 30 mPa·s, measured as a 2 weight-% aqueous solution at 20° C. according to ASTM D2363-79 (Reapproved 2006). Such low viscosity cellulose ethers are particularly useful for the manufacture of capsules or coatings for dosage forms. These cellulose ethers have a lower gelation temperature in aqueous solutions than known hydroxyalkyl methyl celluloses of the same viscosity and concentration in aqueous solutions. The gelation temperature depends on the MS(hydroxyalkyl). It has surprisingly been found that a 20 weight percent aqueous solution of the low viscosity cellulose ether of the present invention, such as hydroxypropyl methylcellulose or hydroxyethyl methylcellulose, generally meets the relationship [(gelation temperature[° C.]/1[° C.])−(150*MS(hydroxyalkyl)]<20, preferably <10, more preferably <0, and most preferably <−5, wherein the gelation temperature is the temperature in ° C. at which G'/G"=1, G' being the storage modulus and G" being the loss modulus of the 20 weight percent aqueous solution of the cellulose ether. No precipitation is detected when heating a 20 weight percent aqueous solution of such low viscosity cellulose ether of the present invention to cause gelation of the aqueous solution.

The storage modulus G', the loss modulus G" and the gelation temperature at which G'/G"=1, each of a 20 weight percent aqueous solution of the cellulose ether are measured in a temperature sweep experiment using an Anton Paar Physica MCR 501 with a peltier temperature control system in oscillation shear flow. A parallel plate (PP-50) geometry with a measurement gap of 1 mm is used. The geometry is covered with a metal ring (inner diameter of 65 mm, width of 5 mm, and height of 15 mm) around the geometry and the outer surface of the solution is covered with paraffin oil. The measurements are performed at a constant frequency of 2 Hz. and a constant strain (deformation amplitude) of 0.5% from 5° C. to 75° C. or −2° C. to 75° C., if 5° C. is already near to the cross-over of G' and U. These measurements are conducted with a heating rate of 1° C./min with a data collection rate of 4 points/min. The storage modulus G', which is obtained from the oscillation measurements, represents the elastic properties of the solution. The loss modulus G", which is obtained from the oscillation measurements, represents the viscous properties of the solution. During the gelation process of the sample, G' exceeds U. The cross-over of G' and G" represents the gelation temperature. Some cellulose ethers of the present invention might show two points of cross-over of G' and G. In such case the gelation temperature is the temperature at which G'/G"=1 and G">G' at a temperature which is 1° C. colder than G'/G"=1.

Methods of making the novel cellulose ethers of the present invention are described in detail in the Examples. Some aspects of the process for making the novel cellulose ethers are described in more general terms below.

Generally speaking, cellulose pulp or, as the reaction of cellulose pulp to the hydroxyalkyl methyl cellulose proceeds, to partially reacted cellulose pulp, is alkalized in two or more stages, preferably in two or three stages, in one or more reactors with an aqueous alkaline solution of an alkali metal hydroxide, more preferably sodium hydroxide. The aqueous alkaline solution preferably has an alkali metal hydroxide content of from 30 to 70 percent, more preferably from 35 to 60 percent, most preferably from 48 to 52 percent, based on the total weight of the aqueous alkaline solution.

In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product.

Typically from 1.2 to 2.0 molar equivalents of alkali metal hydroxide per mole of anhydroglucose units in the cellulose are added in the first stage. Uniform swelling and distribution in the pulp is optionally controlled by mixing and agitation. In the first stage the rate of addition of the alkali metal hydroxide agent is not very critical. It can be added in several portions, e.g., in 2 to 4 portions, or continuously. The temperature at the first stage of contacting the alkali metal hydroxide with the cellulose pulp is typically maintained at or below about 45° C. The first stage of alkalization typically lasts from 15 to 60 minutes.

A methylating agent, such as methyl chloride or dimethyl sulfate is also added to the cellulose pulp, typically after the addition of the alkali metal hydroxide. The total amount of the methylating agent is generally from 2 to 5.3 mols per mole of anhydroglucose units. The methylating agent can be added to the cellulose or, as the reaction of cellulose pulp to the hydroxyalkyl methyl cellulose proceeds, to partially reacted cellulose pulp, in a single stage, but it is preferably added in two or more stages, more preferably two or three stages, most preferably two stages.

If the methylating agent is added in a single stage, it is generally added in an amount of from 3.5 to 5.3 moles of methylating agent per mole of anhydroglucose units, but in any event it is added in at least an equimolar amount, compared to the added total molar amount of alkali metal hydroxide, before heating the reaction mixture. If the methylating agent is added in a single stage, it is preferably added at a rate of from 0.25 to 0.5 molar equivalents of methylating agent per mole of anhydroglucose units per minute.

If the methylating agent is added in two stages, in the first stage it is generally added in an amount of from 2 to 2.5 moles of methylating agent per mole of anhydroglucose units before heating the reaction mixture, but in any event it is added in at least an equimolar amount, compared to the molar amount of alkali metal hydroxide added in the first stage of alkali metal hydroxide addition. If the methylating agent is added in two stages, the methylating agent of the first stage is preferably added at a rate of from, 0.25 to 0.5 molar equivalents of methylating agent per mole of anhydroglucose units per minute. The methylating agent of the single stage or of the first stage may be pre-mixed with the suspending agent. In this case the mixture of suspending agent and methylating agent preferably comprises from 20 to 50 weight percent, more preferably from 30 to 50 weight percent, of the suspending agent, based on the total weight of methylating agent and suspending agent. Once the cellulose has been contacted with the alkali metal hydroxide and methylating agent, the reaction temperature is typically increased over a time period of 30 to 80 minutes, more typically of 50 to 70 minutes, to a temperature of about 70-85° C., preferably about 75-80° C., and reacted at this temperature for 10 to 30 minutes.

If the methylating agent is added in two stages, the second stage of methylating agent is generally added to the reaction mixture after having heated the reaction mixture to a temperature of about 70-85° C. for 10 to 30 minutes. The methylating agent of second stage is generally added in an amount of from 1.5 to 3.4 moles per mole of anhydroglucose units, but in any event it is added in at least an equimolar amount, compared to the molar amount of alkali metal hydroxide present in the reaction mixture. Accordingly, the methylating agent of the second stage, if any, is added to the reaction mixture before or during the second and optionally third stage of alkali metal hydroxide addition in such a manner that the alkali metal hydroxide is not contacted in excess amounts with the cellulose pulp. The methylating agent of the second stage is preferably added at a rate of from 0.25 to 0.5 molar equivalents of methylating agent per mole of anhydroglucose units per minute. If the methylating agent is added in two stages, the molar ratio between the methylating agent of the first stage and the methylating agent of the second stage is generally from 0.68:1 to 1.33:1.

If the alkali metal hydroxide is added in two stages, typically from 1.0 to 2.9 molar equivalents of alkali metal hydroxide per mole of anhydroglucose units are added in the second stage, after the addition of the methylating agent of the single stage or first stage and simultaneously with or after the addition of the methylating agent of the second stage, if any. The molar ratio between the alkali metal hydroxide of the first stage and the alkali metal hydroxide of the second stage generally is from 0.6:1 to 1.2:1. It is important to add the alkali metal hydroxide used in the second stage slowly, i.e., at a rate of less than 0.04, typically at a rate of less than 0.03 molar equivalents of alkali metal hydroxide per mole of anhydroglucose units per minute. The alkali metal hydroxide of the second stage is generally added at a temperature of from 55 to 80° C., preferably from 60 to 80° C.

As an alternative to the procedure above wherein the methylating agent and alkali metal hydroxide each are added in two stages, the methylating agent of the second stage is added to the reaction mixture after a portion of the alkali metal hydroxide of the second stage has been added, followed by subsequent addition of alkali metal hydroxide; i.e., the methylating agent is added in a second stage, which is followed by the addition of a third stage of alkali metal hydroxide. In this embodiment of the process, the total amount of alkali metal hydroxide per mole of anhydroglucose added in the second and third stage is generally 1.0 to 2.9 moles per mole of anhydroglucose units, of which preferably 40 to 60 percent are added in the second stage and 60 to 40 percent are added in the third stage. Preferably the alkali metal hydroxide used in the third stage is added slowly, i.e., at a rate of less than 0.04, typically at a rate of less than 0.03 molar equivalents of alkali metal hydroxide per mole of anhydroglucose units per minute. The methylating agent and alkali metal hydroxide of the third stage are generally added at a temperature of from 55 to 80° C., preferably from 65 to 80° C.

One or more, preferably one or two, hydroxyalkylating agents, such as ethylene oxide and/or propylene oxide are also added to the cellulose pulp, or, as the reaction of cellulose pulp to the hydroxyalkyl methyl cellulose proceeds, to partially reacted cellulose pulp, either before, after, or concurrently with the alkali metal hydroxide added in the first stage. Preferably only one hydroxyalkylating agent is used. The hydroxyalkylating agent is generally added in an amount of 0.2 to 2.0 mole of hydroxyalkylating agent per mole of anhydroglucose units. The hydroxyalkylating agent is advantageously added before heating the reaction mixture to the reaction temperature, i.e. at a temperature of from 30 to 80° C., preferably from 45 to 80° C.

An additional alkylating agent, different from a methylating agent, may also be added to the cellulose pulp, either before, after, or concurrently with the alkali metal hydroxide added in the first stage. A useful alkylating agent is an ethylating agent, such as ethyl chloride. The additional alkylating agent is generally added in an amount of 0.5 to 6 moles of alkylating agent per mole of anhydroglucose units. The alkylating agent is advantageously added before heating the reaction mixture to the reaction temperature, i.e. at a temperature of from 30 to 80° C., preferably from 45 to 80° C.

The cellulose ether is washed to remove salt and other reaction by-products. Any solvent in which salt is soluble may be employed, but water is preferred. The cellulose ether may be washed in the reactor, but is preferably washed in a separate washer located downstream of the reactor. Before or after washing, the cellulose ether may be stripped by exposure to steam to reduce residual organic content.

The cellulose ether is dried to a reduced moisture and volatile content of preferably about 0.5 to about 10.0 weight percent water and more preferably about 0.8 to about 5.0 weight percent water and volatiles, based upon the sum of the weight of cellulose ether and the volatiles. The reduced moisture and volatiles content enables the cellulose ether to be milled into particulate form. The cellulose ether is milled to particulates of desired size. If desired, drying and milling may be carried out simultaneously.

According to the above-mentioned process a cellulose ether is obtained which generally has a viscosity of more than 150 mPa·s, preferably from 500 to 200,000 mPa·s, more preferably from 500 to 100,000 mPa·s, most preferably from 1,000 to 80,000, particularly from 1,000 to 60,000, determined in a 1.5% by weight aqueous solution at 20° C. in a Haake RS600 at a shear rate of 2.55 $s^{-1}$. For preparing a cellulose ether which is particularly suitable for the production of capsules or coatings of dosage forms, such cellulose ether is generally subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent. In such partial depolymerization process a cellulose ether can be obtained which has a viscosity of from 2 to 200 mPa·s, preferably from 2 to 100 mPa·s, more preferably from 2.5 to 50 mPa·s, in particular from 3 to 30 mPa·s, determined in a 2% by weight aqueous solution at 20° C. according to ASTM D2363-79 (Reapproved 2006).

Another aspect of the present invention is an aqueous composition for the manufacture of capsules or coatings of dosage forms which comprises from 7 to 40 weight percent, preferably from 10 to 30 weight percent of the cellulose ether of the present invention, based on the total weight of the aqueous composition. The cellulose ether of the present invention preferably has a viscosity of from 2 to 200 mPa·s, preferably from 2 to 100 mPa·s, more preferably from 2.5 to 50 mPa·s, in particular from 3 to 30 mPa·s, determined in a 2% by weight aqueous solution at 20° C. according to ASTM D2363-79 (Reapproved 2006). The aqueous solution may further comprise optional additives, such as coloring agents, flavor and taste improvers, antioxidants, plasticizers, and surfactants. For example, when producing capsules a water-soluble food dye, such as red oxide, or a natural dye, may be used as a coloring agent; $TiO_2$ may be used as a masking agent; polyethylene glycol, polypropylene glycol, sorbitol or glycerin may be used as a plasticizer or as a surfactant to improve the flexibility of the capsule film. Particularly useful additives for coatings of solid forms are single layer film plasticizers, solids-loading enhancers, a second cellulose ether, surfactants, lubricants, polishing agents, pigments, anti-tack agents, glidants, opacifiers, coloring agents and any combination thereof.

In one aspect of the present invention, the aqueous composition may be used for coating dosage forms, such as tablets, granules, pellets, caplets, lozenges, suppositories, pessaries or implantable dosage forms, to form a coated composition. Preferred dosage forms are pharmaceutical dosage forms, nutrition supplements or agricultural dosage forms. In another aspect of the present invention the aqueous composition may be used for the manufacture of capsules.

One method for the manufacture of capsules is the "hot-pin method". This method preferably comprises the steps of (a)

providing an aqueous composition comprising the above-mentioned cellulose ether and optional additives, (b) preheating dipping pins so that they are at a temperature above the gelation temperature of the aqueous composition when dipped into the aqueous composition, (c) dipping the preheated dipping pins into the aqueous composition maintained at a temperature below its gelation temperature, (d) withdrawing the dipping pins from the aqueous composition obtaining a film on the dipping pins, and (e) drying the film on the dipping pins at a temperature above the gelation temperature of the aqueous composition so as to obtain molded capsule shells on the pins. In this hot-pin method, the dipping pins are preferably preheated so that they are at a temperature of 55 to 95° C., preferably of 60 to 90° C. when dipped into the aqueous composition. The pre-heated dipping pins are dipped into the aqueous composition that is preferably maintained at a temperature of 10° C. to 1° C., more preferably 4° C. to 1° C. below its gelation temperature. The hot-pin method used to prepare capsules from the aqueous composition of the cellulose ether is described in detail in the International Patent Publication No. WO 2008/050209.

Another method for the manufacture of capsules is the "cold-pin method". In this method an aqueous composition comprising the above-mentioned cellulose ether and additionally a gelling agent such as carrageenan, pectin, gellan gum, or another sequestering agent or gelling aid, such as potassium, magnesium, ammonium, or calcium ions. In the cold-pin method pins are generally kept at room temperature and are dipped into the aqueous composition maintained at a temperature above its gelation temperature, preferably at a temperature of 45 to 60° C., the dipping pins are withdrawn from the aqueous composition and a film is obtained on the dipping pins, and the film is dried on the dipping pins to obtain molded capsule shells on the pins. The cold-pin method used to prepare capsules from the aqueous composition of the cellulose ether is described in detail in European Patent Application No. EP 0 714 656 and in U.S. Pat. No. 6,410,050. Usage of the cellulose ethers of the present invention, which have a lower gelation temperature in an aqueous solution than comparable known hydroxyalkyl methylcelluloses, also provides advantages in the "cold-pin method". When cellulose ethers of the present invention are incorporated in the aqueous composition, the cellulose ethers of the present invention tend to gel more readily than known hydroxyalkyl methylcelluloses as the cellulose ethers of the present invention exhibit a smaller difference between gelation temperature and pin temperature (e.g., room temperature) than known hydroxyalkyl methylcelluloses of the same substitution kind and level. Thus fewer amounts or even no gelling agent are needed for producing capsules using cellulose ethers of the present invention having a low temperature.

This will simplify manufacturing process, improve capsule appearance (clarity and gloss), and potentially reduce disintegration time of capsules especially compared to capsules with gellan as gelling agent (reference: Cole E. T., Scott, R. A., Cade, D., Connor, A. L. and Wilding, I. R., Pharm. Res., 2004, 21, 793-798) or without gelling agent.

EXAMPLES

Examples 1-15 and Comparative Examples A to D

High Viscosity Cellulose Ethers

The following examples are for illustrative purposes only and are not intended to limit the scope of the present invention. All percentages are by weight unless otherwise specified.

To achieve homogenous solutions, 3 g of the cellulose ether powder (under consideration of the water content of the cellulose ether) is suspended in 197 g water at 70° C. with an overhead laboratory stirrer at 700 rpm for 10 min. These solutions are then cooled to a temperature of 2° C. for 5 hours to complete the dissolution process. During these 5 hours the solutions are stirred at 500-1000 rpm and lost water due to evaporation is replaced. These solutions are then stored in a refrigerator over night. Prior to the analysis the cold solutions are stirred for 15 min at 100 rpm.

The viscosities of the hydroxypropyl methylcellulose is determined in a 1.5% by weight aqueous solution at 20° C. in a Haake RS600 rheometer with a cone and plate Geometry (CP-60/2°) at 20° C. and at a shear rate of 2.55 $s^{-1}$.

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The DS(methyl) and MS (hydroxyethyl) in hydroxyethyl methylcellulose is effected by Zeisel cleavage with hydrogen iodide followed by gas chromatography. (G. Bartelmus and R. Ketterer, Z. Anal. Chem. 286 (1977) 161-190).
Determination of s23/s26

The determination of ether substituents in cellulose ethers is generally known and e.g., described in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 is conducted as follows: 10-12 mg of the cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the cellulose ether is performed using a dry nitrogen atmosphere in a 4 mL screw cap vial. After solubilization the dissolved cellulose ether is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 µL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 µL of acetic anhydride and 150 µL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 µm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 µL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN Increments Used for ECN Calculations:

| Type of carbon atom | ECN increment |
|---|---|
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of s23/s26.

MRFmonomer=ECN2,3,6-Me/ECNmonomer

The mole fractions of the monomers are calculated by dividing the corrected peak areas by the total corrected peak area according to the following formulas:

$$s23=[(23\text{-Me}+23\text{-Me-6-HAMe}+23\text{-Me-6-HA}+23\text{-Me-6-HAHAMe}+23\text{-Me-6-HAHA}]; \text{ and}$$

$$s26=[(26\text{-Me}+26\text{-Me-3-HAMe}+26\text{-Me-3-HA}+26\text{-Me-3-HAHAMe}+26\text{-Me-3-HAHA}], \text{ wherein}$$

s23 is the sum of the molar fractions of anhydroglucose units which meet the following conditions:
a) the two hydroxy groups in the 2- and 3-positions of the anhydroglucose unit are substituted with methyl groups and the 6-position is not substituted (=23-Me);
b) the two hydroxy groups in the 2- and 3-positions of the anhydroglucose unit are substituted with methyl groups and the 6-position is substituted with methylated hydroxyalkyl (=23-Me–6-HAMe) or with a methylated side chain comprising 2 hydroxyalkyl groups (=23-Me–6-HAHAMe); and
c) the two hydroxy groups in the 2- and 3-positions of the anhydroglucose unit are substituted with methyl groups and the 6-position is substituted with hydroxyalkyl (=23-Me–6-HA) or with a side chain comprising 2 hydroxyalkyl groups (=23-Me–6-HAHA). s26 is the sum of the molar fractions of anhydroglucose units which meet the following conditions:
a) the two hydroxy groups in the 2- and 6-positions of the anhydroglucose unit are substituted with methyl groups and the 3-position is not substituted (=26-Me);
b) the two hydroxy groups in the 2- and 6-positions of the anhydroglucose unit are substituted with methyl groups and the 3-position is substituted with methylated hydroxyalkyl (=26-Me–3-HAMe) or with a methylated side chain comprising 2 hydroxyalkyl groups (=26-Me–3-HAHAMe); and
c) the two hydroxy groups in the 2- and 6-positions of the anhydroglucose unit are substituted with methyl groups and the 3-position is substituted with hydroxyalkyl (=26-Me–3-HA) or with a side chain comprising 2 hydroxyalkyl groups (=26-Me–3-HAHA).

The results of the determination of the substituents in the HAMC are listed in Table 4 below. In the case of HPMC's hydroxyalkyl (HA) is hydroxypropyl (HP) and methylated hydroxyalkyl (HAMe) is methylated hydroxypropyl (HPMe).

Determination of Storage Modulus G', Loss Modulus G", Gelation Temperature t and Gel Strength To characterize the temperature dependent properties of the precipitation or gelation of a 1.5 weight percent aqueous cellulose ether solution, an Anton Paar Physica MCR 501 rheometer (Ostfildern, Germany) with a Cup & Bob set-up (CC-27) and a peltier temperature control system is used in oscillation shear flow. These solutions are prepared according to the same dissolution procedure as described for the viscosity measurements. The measurements are performed at a constant frequency of 2 Hz. and a constant strain (deformation amplitude) of 0.5% from 10° C. to 85° C. with a heating rate of 1° C./min with a data collection rate of 4 points/min. The storage modulus G', which is obtained from the oscillation measurements, represents the elastic properties of the solution. The loss modulus G", which is obtained from the oscillation measurements, represents the viscous properties of the solution. At low temperature the loss modulus values G' are higher than the storage modulus G' and both values are slightly decreasing with increasing temperatures. If a precipitation takes places at elevated temperatures the storage modulus drops down. This precipitation temperature is analyzed from a plot of the log storage modulus G' vs. temperature as the cross over of two tangent. The first tangent is fitted to the decrease of the storage modulus with increasing temperatures and the second tangent is fitted to the drop of the storage modulus over a temperature region of 1-3° C. With further increasing temperatures the storage modulus values are increasing and a cross-over between the storage modulus and the loss modulus is obtained. The cross-over of G' and G" is determined to be the gelation temperature. Some cellulose ethers of the present invention might show two points of cross-over of G' and U. In such case the gelation temperature is the temperature at which G'/G"=1 and G">G' at a temperature which is 1° C. colder than G'/G"=1. FIG. 1 illustrates how to determine the precipitation temperature and the gelation temperature of a cellulose ether of the present invention; the results for Example 2 are illustrated in FIG. 1.

Example 1

Hydroxypropyl methylcellulose (HPMC) is produced according to the following procedure. Finely ground wood cellulose pulp is loaded into a jacketed, agitated reactor. The reactor is evacuated and purged with nitrogen to remove oxygen and then evacuated again. The reaction is carried out in two stages. In the first stage a 50 weight percent aqueous solution of sodium hydroxide is sprayed onto the cellulose in an amount of 2.0 moles of sodium hydroxide per mole of anhydroglucose units in the cellulose and the temperature is adjusted to 40° C. After stirring the mixture of aqueous sodium hydroxide solution and cellulose for about 20 minutes at 40° C., 1.5 moles of dimethyl ether, 2.5 moles of methyl chloride and 0.6 mols of propylene oxide per mole of anhydroglucose units are added to the reactor. The contents of the reactor are then heated in 60 min to 80° C. After having reached 80° C., the first stage reaction is allowed to proceed for 30 min.

The second stage of the reaction is started by addition of methyl chloride in an amount of 2.8 molar equivalents of methyl chloride per mole of anhydroglucose units. The addition time for methyl chloride is 10 min. Then a 50 weight percent aqueous solution of sodium hydroxide at an amount of 2.3 moles of sodium hydroxide per mole of anhydroglucose units is added over a time period of 90 min. The rate of addition is 0.026 moles of sodium hydroxide per mole of anhydroglucose units per minute. After the second stage addition is completed the contents of there reactor are then kept at a temperature of 80° C. for 120 min.

After the reaction, the reactor is vented and cooled down to about 50° C. The contents of the reactor are removed and transferred to a tank containing hot water. The crude HPMC is then neutralized with formic acid and washed chloride free with hot water (assessed by $AgNO_3$ flocculation test), cooled to room temperature and dried at 55° C. in an air-swept drier. The material is then ground using an Alpine UPZ mill using a 0.5 mm screen.

Example 2

Example 1 is repeated, except the amount of propylene oxide added to the reaction mixture is 0.8 mols of propylene oxide per mole of anhydroglucose units.

Example 3

Example 1 is repeated, except the amount of propylene oxide added to the reaction mixture is 0.2 mols of propylene oxide per mole of anhydroglucose units.

Example 4

Example 1 is repeated, except the amount of propylene oxide added to the reaction mixture is 0.4 mols of propylene oxide per mole of anhydroglucose units.

Example 5

Example 1 is repeated, except the amount of propylene oxide added to the reaction mixture is 1.15 mols of propylene oxide per mole of anhydroglucose units.

Example 6

Example 1 is repeated, except the amount of propylene oxide added to the reaction mixture is 1.4 mols of propylene oxide per mole of anhydroglucose units.

Example 7

Example 1 is repeated, except the amount of sodium hydroxide in the first stage is 1.2 mols per mole of anhydroglucose units, the amount of methyl chloride in the first stage is 2.0 mols per mole of anhydroglucose units, the amount of sodium hydroxide in the second stage is 1.0 mols per mole of anhydroglucose units, the amount of methyl chloride in the second stage is 1.5 mols per mole of anhydroglucose units and the amount of propylene oxide added to the reaction mixture is 0.2 mols of propylene oxide per mole of anhydroglucose units.

Example 8

Example 1 is repeated, except the amount of sodium hydroxide in the first stage is 1.2 mols per mole of anhydroglucose units, the amount of methyl chloride in the first stage is 2.0 mols per mole of anhydroglucose units, the amount of sodium hydroxide in the second stage is 1.0 mols per mole of anhydroglucose units, the amount of methyl chloride in the second stage is 1.5 mols per mole of anhydroglucose units and the amount of propylene oxide added to the reaction mixture is 0.4 mols of propylene oxide per mole of anhydroglucose units.

Example 9

Example 1 is repeated, except the amount of sodium hydroxide in the first stage is 1.2 mols per mole of anhydroglucose units, the amount of methyl chloride in the first stage is 3.5 mols per mole of anhydroglucose units, the amount of sodium hydroxide in the second stage is 1.0 mols per mole of anhydroglucose units, the amount of methyl chloride in the second stage is 0 (zero) mols per mole of anhydroglucose units and the amount of propylene oxide added to the reaction mixture is 1.0 mols of propylene oxide per mole of anhydroglucose units.

Example 10

Example 1 is repeated, except the amount of sodium hydroxide in the first stage is 1.2 mols per mole of anhydroglucose units, the amount of methyl chloride in the first stage is 3.5 mols per mole of anhydroglucose units, the amount of sodium hydroxide in the second stage is 1.0 mols per mole of anhydroglucose units, the amount of methyl chloride in the second stage is 0 (zero) mols per mole of anhydroglucose units and the amount of propylene oxide added to the reaction mixture is 1.35 mols of propylene oxide per mole of anhydroglucose units.

Example 11

Hydroxypropyl methylcellulose is produced according to the following procedure. Finely ground wood cellulose pulp is loaded into a jacketed, agitated reactor. The reactor is evacuated and purged with nitrogen to remove oxygen and then evacuated again. The reaction is carried out in three stages. In the first stage a 50 weight percent aqueous solution of sodium hydroxide is sprayed onto the cellulose in an amount of 1.8 moles of sodium hydroxide per mole of anhydroglucose units in the cellulose and the temperature is adjusted to 40° C. After stirring the mixture of aqueous sodium hydroxide solution and cellulose for about 10-20 minutes at 40° C., 1.5 mols of dimethyl ether, 2.3 mols of methyl chloride and 0.4 mols of propylene oxide per mole of anhydroglucose units are added to the reactor. The contents of the reactor are then heated in 60 min to 80° C. After having reached 80° C., the first stage reaction is allowed to proceed for 5 min. Then the content of the reactor is cooled down in 25 min to 65° C.

The second stage reaction is started by addition of a 50 weight percent aqueous solution of sodium hydroxide at an amount of 1.45 moles of sodium hydroxide per mole of anhydroglucose units over a time period of 45 min. The rate of addition is 0.032 moles of sodium hydroxide per mole of anhydroglucose units per minute, followed by addition of methyl chloride in an amount of 3.4 moles of methyl chloride per mole of anhydroglucose units. The addition time for methyl chloride is 10 min.

Then, as a third stage, again a 50 weight percent aqueous solution of sodium hydroxide at an amount of 1.45 moles of sodium hydroxide per mole of anhydroglucose units is added over a time period of 45 min. After the third stage of sodium hydroxide addition has been completed, the contents of the reactor are then heated up to 80° C. in 15-30 min and kept at this temperature for 90 min.

The produced cellulose ether is further processed as described in Example 1.

Example 12

Example 1 is repeated, except ethylene oxide is added to the reaction mixture instead of propylene oxide. The amount of ethylene oxide added is 0.2 mols of ethylene oxide per mole of anhydroglucose units.

Example 13

Example 1 is repeated, except ethylene oxide is added to the reaction mixture instead of propylene oxide. The amount of ethylene oxide added is 0.4 mols of ethylene oxide per mole of anhydroglucose units.

Example 14

Example 1 is repeated, except ethylene oxide is added to the reaction mixture instead of propylene oxide. The amount of ethylene oxide added is 0.6 mols of ethylene oxide per mole of anhydroglucose units.

Example 15

Example 1 is repeated, except ethylene oxide is added to the reaction mixture instead of propylene oxide. The amount of ethylene oxide added is 0.8 mols of ethylene oxide per mole of anhydroglucose units.

The properties of the hydroxypropyl methyl celluloses (HPMC) and hydroxyethyl methyl celluloses (HEMC) of Examples 1 to 15 and of Comparative Examples A to D are listed in Table 1 below. The hydroxypropyl methyl cellulose and hydroxyethyl methyl celluloses of Comparative Examples A to D are commercially available from The Dow Chemical Company.

TABLE 1

(HPMC)

| (Comparative) Example | DS (methyl) | MS (hydroxypropyl) | Viscosity at 20° C.[1] [mPa·s] | s23/s26- 0.2 * MS(hydroxypropyl) | Precipitation Temperature, [° C.][1] | Gelation Temperature, G'/G" = 1, [° C.][1] | Gelation temp. minus Precipitation temp., [° C.][1] | Loss Modulus G" at 80° C., [Pa][1] | Storage Modulus G' at 80° C., [Pa][1] |
|---|---|---|---|---|---|---|---|---|---|
| 1 | 1.82 | 0.20 | 9110 | 0.18 | — | 55 | 0 | 22.7 | 1200 |
| 2 | 1.83 | 0.28 | 7691 | 0.16 | 59 | 61 | 2 | 10.6 | 431 |
| 3 | 1.8 | 0.08 | 8225 | 0.18 | — | 42.2 | 0 | 36.8 | 1810 |
| 4 | 1.81 | 0.15 | 7753 | 0.19 | — | 50 | 0 | 25.9 | 1450 |
| 5 | 1.83 | 0.38 | 4858 | 0.19 | 58 | 60.2 | 2.2 | 7.03 | 248 |
| 6 | 1.86 | 0.44 | 5575 | 0.19 | 57 | 59 | 2 | 9.47 | 237 |
| 7 | 1.43 | 0.10 | 1483 | 0.16 | — | 43.2 | 0 | 21.2 | 881 |
| 8 | 1.44 | 0.19 | 3746 | 0.16 | — | 39.5 | 0 | 8.53 | 493 |
| 9 | 1.38 | 0.27 | 3792 | 0.16 | — | 40 | 0 | 5.45 | 317 |
| 10 | 1.40 | 0.33 | 4316 | 0.17 | — | 41.7 | 0 | 5.87 | 268 |
| 11 | 2.06 | 0.17 | 1866 | 0.21 | — | 56.5 | 0 | 45.9 | 1340 |
| A | 1.90 | 0.14 | 6087 | 0.38 | 59 | 66.7 | 7.7 | 0.761 | 13.6 |
| B | 1.84 | 0.24 | 4805 | 0.36 | 57 | 65.5 | 8.5 | 0.86 | 9.1 |
| 12 | 1.81 | 0.14 | 6375 | 0.22 | — | 44.2 | 0 | 2170 | 30.9 |

TABLE 1-continued (HPMC)

| (Comparative) Example | DS (methyl) | MS (hydroxy-propyl) | Viscosity at 20° C.[1] [mPa·s] | s23/s26- 0.2 * MS(hydroxypropyl) | Precipitation Temperature, [° C.][1] | Gelation Temperature, G'/G" = 1, [° C.][1] | Gelation temp. minus Precipitation temp., [° C.][1] | Loss Modulus G" at 80° C., [Pa][1] | Storage Modulus G' at 80° C., [Pa][1] |
|---|---|---|---|---|---|---|---|---|---|
| 13 | 1.84 | 0.25 | 5827 | 0.24 | — | 53.2 | 0 | 673 | 9.64 |
| 14 | 1.87 | 0.38 | 4946 | 0.25 | — | 60.2 | 0 | 182 | 5.88 |
| 15 | 1.92 | 0.66 | 4916 | 0.27 | — | 71.5 | 0 | 54 | 5.74 |
| C | 1.80 | 0.22 | 17380 | 0.416 | 68.3 | 72.4 | 4.1 | 36.5 | 4.45 |
| D | 1.83 | 0.42 | 15240 | 0.405 | 70.8 | 73.3 | 2.5 | 21.1 | 2.16 |

[1]measured as 1.5 weight percent aqueous solution

Examples 16 to 21 and Comparative Examples E to F

Low Viscosity Cellulose Ethers

A 20 weight percent aqueous solution of hydroxypropyl methylcellulose (HPMC) is produced by dispersing the HPMC at 60-65° C. and cooling the dispersion to 1-5° C., stirring it at about 500 rpm for at least 2 hours at 1-5° C. and keeping it over night in a refrigerator at 1-5° C. The solution is stirred for 5 min at 100 rpm before determining the storage modulus G', the loss modulus G", and the gelation temperature at which G'/G"=1.

The storage modulus G', the loss modulus G" and the gelation temperature at which G'/G"=1, each of a 20 weight percent aqueous solution of the hydroxypropyl methylcellulose (HPMC) are measured in a temperature sweep experiment using an Anton Paar Physica MCR 501 with a peltier temperature control system in oscillation shear flow. A parallel plate (PP-50) geometry with a measurement gap of 1 mm is used. The geometry is covered with a metal ring (inner diameter of 65 mm, width of 5 mm, and height of 15 mm) around the geometry and the outer surface of the solution is covered with paraffin oil. The measurements are performed at a constant frequency of 2 Hz. and a constant strain (deformation amplitude) of 0.5% from 5° C. to 75° C. or −2° C. to 75° C., if 5° C. is already near to the cross-over of G' and U. These measurements are conducted with a heating rate of 1° C./min with a data collection rate of 4 points/min.

The storage modulus G', which is obtained from the oscillation measurements, represents the elastic properties of the solution. The loss modulus G", which is obtained from the oscillation measurements, represents the viscous properties of the solution. During the gelation process of the sample, G' exceeds U. The cross-over of G' and G" represents the gelation temperature.

The viscosity of the samples is measured as a 2% by weight aqueous solution at 20° C. according to ASTM D2363-79 (Reapproved 2006).

Examples 16-21

Hydroxypropyl methylcellulose of Examples 1-6 are partially depolymerized by heating the powderous samples with gaseous hydrogen chloride at a time and temperature listed in Table 2 below. The partially depolymerized hydroxypropyl methylcellulose is neutralized with sodium bicarbonate.

TABLE 2

| | Example | | | | | |
|---|---|---|---|---|---|---|
| | 16 | 17 | 18 | 19 | 20 | 21 |
| Feedstock material Example | 1 | 2 | 3 | 4 | 5 | 6 |
| Moisture Content of powderous Feedstock [%] | 3 | 3 | 3.5 | 3.9 | 3.2 | 3.3 |
| Weight in g of HCl, based on weight in kg of feedstock material | 3 | 3 | 3 | 3 | 3 | 3 |
| degradation time [min] | 210 | 210 | 210 | 210 | 210 | 210 |
| Degradation temp. [° C.] | 80 | 80 | 80 | 80 | 80 | 80 |
| Viscosity as 2 wt. % aqueous solution at 20° C. [m·Pas] | 4 | 5.5 | 4.7 | 3.8 | 4.7 | 4.7 |

Comparative Example E

This Comparative Example is a hydroxypropyl methylcellulose having a DS(methyl) of 1.90, an MS (hydroxypropyl) of 0.14 and a viscosity of 5.5 mPa·s as 2 wt. % aqueous solution at 20° C. A DS(methyl) of 1.90 and an MS (hydroxypropyl) of 0.14 corresponds to a methoxy content of 29.9% (w/w) and a hydroxypropoxy content of 5.3% (w/w). This hydroxypropyl methylcellulose corresponds to the ones disclosed in WO 2008/050209 for the manufacture of hard capsules. It is commercially available from The Dow Chemical Company and obtained after partial depolymerization of Comparative Example A as described for Examples 12-17.

Comparative Example F

This Comparative Example is a hydroxypropyl methylcellulose having a DS(methyl) of 1.84, an MS (hydroxypropyl) of 0.24 and a viscosity of 6.3 mPa·s as 2 wt. % aqueous solution at 20° C. A DS(methyl) of 1.84 and an MS (hydroxypropyl) of 0.25 corresponds to a methoxy content of 28.3% (w/w) and a hydroxypropoxy content of 8.9% (w/w).

It is available from The Dow Chemical Company and obtained after partial depolymerization of Comparative Example B as described for Examples 12-17.

The gelation temperatures are listed in Table 3 below.

TABLE 3

| (Comparative) Example | [s23/s26- 0.2 * MS(hydroxy-alkyl)] | DS (methyl) | MS (hydroxy-propyl) | Viscosity at 20° C. [mPa·s][1] | Gelation temperature [° C.][2] | (gelation temp. [° C.]/1[° C.])-(150 * MS(hydroxyalkyl) |
|---|---|---|---|---|---|---|
| 16 | 0.18 | 1.82 | 0.20 | 4.0 | 14.2 | −15.8 |
| 17 | 0.16 | 1.83 | 0.28 | 5.5 | 28.7 | −13.3 |

TABLE 3-continued

| (Comparative) Example | [s23/s26-0.2 * MS(hydroxy-alkyl)] | DS (methyl) | MS (hydroxy-propyl) | Viscosity at 20° C. [mPa·s][1] | Gelation temperature [° C.][2] | (gelation temp. [° C.]/1[° C.])-(150 * MS(hydroxyalkyl) |
|---|---|---|---|---|---|---|
| 18 | 0.18 | 1.80 | 0.08 | 4.7 | <0° C. | — |
| 19 | 0.19 | 1.81 | 0.15 | 3.8 | 1.2 | −21.3 |
| 20 | 0.19 | 1.83 | 0.38 | 4.7 | 41.5 | −15.5 |
| 21 | 0.18 | 1.86 | 0.44 | 4.7 | 56.2 | −9.8 |
| E | 0.38 | 1.90 | 0.14 | 5.5 | 43.5 | 22.5 |
| F | 0.36 | 1.84 | 0.24 | 6.3 | 57.5 | 21.5 |

[1] measured as 2 weight percent aqueous solution
[2] measured as 20 weight percent aqueous solution

TABLE 4

| (HPMC) | | | | | | | | |
|---|---|---|---|---|---|---|---|---|
| | (Comparative) Example | | | | | | | |
| | 1 | 2 | 3 | 4 | 5 | 6 | A | B |
| DS (USP) | 1.82 | 1.83 | 1.8 | 1.81 | 1.83 | 1.86 | 1.90 | 1.84 |
| MS (USP) | 0.2 | 0.28 | 0.08 | 0.15 | 0.38 | 0.44 | 0.14 | 0.24 |
| mol fraction (26-Me) | 0.2861 | 0.2709 | 0.3215 | 0.2984 | 0.2374 | 0.2251 | 0.2409 | 0.2217 |
| mol fraction (26-Me-3-HA) | 0.0161 | 0.0218 | 0.0056 | 0.0124 | 0.0316 | 0.0350 | 0.0091 | 0.0156 |
| mol fraction (26-Me-3-HAHA) | 0.0000 | 0.0000 | 0.0000 | 0.0000 | 0.0000 | 0.0000 | 0.0000 | 0.0000 |
| mol fraction (26-Me-3HAMe) | 0.0022 | 0.0034 | 0.0011 | 0.0019 | 0.0020 | 0.0021 | 0.0013 | 0.0019 |
| mol fraction (26-Me-3HAHAMe) | 0.0000 | 0.0000 | 0.0000 | 0.0000 | 0.0000 | 0.0000 | 0.0000 | 0.0000 |
| mol fraction (23-Me) | 0.0572 | 0.0542 | 0.0618 | 0.0600 | 0.0522 | 0.0506 | 0.0943 | 0.0847 |
| mol fraction (23-Me-6-HA) | 0.0091 | 0.0108 | 0.0019 | 0.0074 | 0.0202 | 0.0226 | 0.0089 | 0.0132 |
| mol fraction (23-Me-6-HAHA) | 0.0000 | 0.0000 | 0.0000 | 0.0000 | 0.0000 | 0.0000 | 0.0000 | 0.0000 |
| mol fraction (23-Me-6-HAMe) | 0.0000 | 0.0000 | 0.0000 | 0.0000 | 0.0000 | 0.0000 | 0.0000 | 0.0000 |
| mol fraction (23-Me-6-HAHAMe) | 0.0000 | 0.0000 | 0.0000 | 0.0000 | 0.0000 | 0.0000 | 0.0000 | 0.0000 |
| S23/s26 | 0.22 | 0.22 | 0.19 | 0.22 | 0.27 | 0.28 | 0.41 | 0.41 |
| S23/s26-0.2 * MS | 0.18 | 0.16 | 0.18 | 0.19 | 0.19 | 0.19 | 0.38 | 0.36 |

| | (Comparative) Example | | | | | | |
|---|---|---|---|---|---|---|---|
| | 7 | 8 | 9 | 10 | 11 | A | B |
| DS (USP) | 1.43 | 1.44 | 1.38 | 1.4 | 2.06 | 1.90 | 1.84 |
| MS (USP) | 0.1 | 0.19 | 0.27 | 0.33 | 0.17 | 0.14 | 0.24 |
| mol fraction (26-Me) | 0.2784 | 0.2615 | 0.2503 | 0.2352 | 0.2811 | 0.2409 | 0.2217 |
| mol fraction (26-Me-3-HA) | 0.0067 | 0.0123 | 0.0160 | 0.0197 | 0.0127 | 0.0091 | 0.0156 |
| mol fraction (26-Me-3-HAHA) | 0.0000 | 0.0000 | 0.0000 | 0.0000 | 0.0000 | 0.0000 | 0.0000 |
| mol fraction (26-Me-3HAMe) | 0.0002 | 0.0006 | 0.0021 | 0.0024 | 0.0027 | 0.0013 | 0.0019 |
| mol fraction (26-Me-3HAHAMe) | 0.0000 | 0.0000 | 0.0000 | 0.0000 | 0.0000 | 0.0000 | 0.0000 |
| mol fraction (23-Me) | 0.0470 | 0.0461 | 0.0479 | 0.0475 | 0.0654 | 0.0943 | 0.0847 |
| mol fraction (23-Me-6-HA) | 0.0051 | 0.0089 | 0.0099 | 0.0132 | 0.0084 | 0.0089 | 0.0132 |
| mol fraction (23-Me-6-HAHA) | 0.0000 | 0.0000 | 0.0000 | 0.0000 | 0.0000 | 0.0000 | 0.0000 |
| mol fraction (23-Me-6-HAMe) | 0.0000 | 0.0000 | 0.0000 | 0.0000 | 0.0000 | 0.0000 | 0.0000 |
| mol fraction (23-Me-6-HAHAMe) | 0.0000 | 0.0000 | 0.0000 | 0.0000 | 0.0000 | 0.0000 | 0.0000 |
| s23/s26 | 0.18 | 0.20 | 0.22 | 0.24 | 0.25 | 0.41 | 0.41 |
| S23/s26-0.2 * MS | 0.16 | 0.16 | 0.16 | 0.17 | 0.21 | 0.38 | 0.36 |

TABLE 4-continued (HPMC)

| | (Comparative) Example | | | | | |
|---|---|---|---|---|---|---|
| | 12 | 13 | 14 | 15 | C | D |
| DS (Zeisel) | 1.81 | 1.84 | 1.87 | 1.92 | 1.8 | 1.83 |
| MS (Zeisel) | 0.14 | 0.25 | 0.38 | 0.66 | 0.22 | 0.42 |
| mol fraction (26-Me) | 0.2990 | 0.2734 | 0.2509 | 0.2138 | 0.2232 | 0.2015 |
| mol fraction (26-Me-3-HA) | 0.0033 | 0.0052 | 0.0069 | 0.0091 | 0.0066 | 0.0098 |
| mol fraction (26-Me-3-HAHA) | 0.0000 | 0.0000 | 0.0000 | 0.0000 | 0.0000 | 0.0000 |
| mol fraction (26-Me-3HAMe) | 0.0036 | 0.0055 | 0.0072 | 0.0089 | 0.0059 | 0.0083 |
| mol fraction (26-Me-3HAHAMe) | 0.0005 | 0.0008 | 0.0010 | 0.0014 | 0.0008 | 0.0014 |
| mol fraction (23-Me) | 0.0584 | 0.0562 | 0.0519 | 0.0473 | 0.0822 | 0.0690 |
| mol fraction (23-Me-6-HA) | 0.0039 | 0.0061 | 0.0083 | 0.0118 | 0.0064 | 0.0109 |
| mol fraction (23-Me-6-HAHA) | 0.0001 | 0.0002 | 0.0004 | 0.0030 | 0.0002 | 0.0005 |
| mol fraction (23-Me-6-HAMe) | 0.0129 | 0.0195 | 0.0259 | 0.0340 | 0.0203 | 0.0282 |
| mol fraction (23-Me-6-HAHAMe) | 0.0001 | 0.0001 | 0.0002 | 0.0019 | 0.0000 | 0.0007 |
| s23/s26 (O—Me) | 0.25 | 0.29 | 0.33 | 0.42 | 0.46 | 0.49 |
| s23/s26-0.2 * MS | 0.22 | 0.24 | 0.25 | 0.29 | 0.42 | 0.41 |

What is claimed is:

1. A cellulose ether wherein
the ether substituents are methyl groups, hydroxyalkyl groups, and optionally alkyl groups being different from methyl,
the cellulose ether has an MS(hydroxyalkyl) of 0.05 to 1.00, and
hydroxy groups of anhydroglucose units are substituted with methyl groups such that [s23/s26−0.2*MS(hydroxyalkyl)] is 0.30 or less,
wherein MS(hydroxyalkyl) is the average number of hydroxyalkyl groups which are bound by an ether bond per mole of anhydroglucose unit,
wherein s23 is the molar fraction of anhydroglucose units wherein only the two hydroxy groups in the 2- and 3-positions of the anhydroglucose unit are substituted with methyl groups and
wherein s26 is the molar fraction of anhydroglucose units wherein only the two hydroxy groups in the 2- and 6-positions of the anhydroglucose unit are substituted with methyl groups and
the cellulose ether has a viscosity of from 2 to 200 mPa·s according to ASTM D2363-79, measured as a 2 wt.-% weight solution in water at 20° C.

2. The cellulose ether of claim 1 being a hydroxyalkyl methyl cellulose.

3. The cellulose ether of claim 2 being a hydroxypropyl methylcellulose and [s23/s26−0.2*MS(hydroxyalkyl)] being 0.27 or less.

4. The cellulose ether of claim 3 having a DS(methyl) of 1.2 to 2.2, wherein DS(methyl) is the average number of OH groups substituted with methyl groups per anhydroglucose unit and wherein a 20 weight percent aqueous solution of the cellulose ether meets the equation $$[(\text{gelation temperature}[° C.]/1[° C.])-(150*MS(\text{hydroxyalkyl}))]<20,$$

wherein the gelation temperature is the temperature at which G'/G"=1,
G' being the storage modulus and G" being the loss modulus of the 20 weight percent aqueous solution of the cellulose ether.

5. The cellulose ether of claim 2 being a hydroxyethyl methylcellulose and [s23/s26−0.2*MS(hydroxyalkyl)] being 0.27 or less.

6. The cellulose ether of claim 1 having a DS(methyl) of 1.2 to 2.2, wherein DS(methyl) is the average number of OH groups substituted with methyl groups per anhydroglucose unit.

7. The cellulose ether of claim 1 wherein a 20 weight percent aqueous solution of the cellulose ether meets the equation $$[(\text{gelation temperature}[° C.]/1[° C.])-(150*MS(\text{hydroxyalkyl}))]<10,$$

wherein the gelation temperature is the temperature at which G'/G"=1,
G' being the storage modulus and G" being the loss modulus of the 20 weight percent aqueous solution of the cellulose ether.

8. A capsule shell comprising the cellulose ether of claim 1.

9. A capsule comprising the capsule shell of claim 8.

10. A process for the manufacture of capsules comprising the step of contacting an aqueous composition comprising the cellulose ether of claim 1 with dipping pins.

11. A process for coating a dosage form comprising the step of contacting an aqueous composition comprising the cellulose ether of claim 1 with the dosage form.

12. An aqueous composition for the manufacture of capsules or coatings of dosage forms comprising from 7 to 40 weight percent of a cellulose ether, based on the total weight of the aqueous composition,
wherein in the cellulose ether
the ether substituents are methyl groups, hydroxyalkyl groups, and optionally alkyl groups being different from methyl, the cellulose ether has an MS(hydroxyalkyl) of 0.05 to 1.00, and hydroxy groups of anhydroglucose units are substituted with methyl groups such that [s23/s26−0.2*MS(hydroxyalkyl)] is 0.30 or less, wherein MS(hydroxyalkyl) is the average number of hydroxyalkyl groups which are bound by an ether bond per mole of anhydroglucose unit, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups and the cellulose ether has a viscosity of from 2 to 200 mPa·s according to ASTM D2363-79, measured as a 2 wt.-% weight solution in water at 20° C.

13. A dosage form being coated with a composition comprising a cellulose ether wherein in the cellulose ether the ether substituents are methyl groups, hydroxyalkyl groups, and optionally alkyl groups being different from methyl, the cellulose ether has an MS(hydroxyalkyl) of 0.05 to 1.00, and hydroxy groups of anhydroglucose units are substituted with methyl groups such that [s23/s26−0.2*MS(hydroxyalkyl)] is 0.30 or less, wherein MS(hydroxyalkyl) is the average number of hydroxyalkyl groups which are bound by an ether bond per mole of anhydroglucose unit, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups and the cellulose ether has a viscosity of from 2 to 200 mPa·s according to ASTM D2363-79, measured as a 2 wt.-% weight solution in water at 20° C.

* * * * *